(12) United States Patent
Itsuki et al.

(10) Patent No.: US 6,355,097 B2
(45) Date of Patent: Mar. 12, 2002

(54) ORGANIC TITANIUM COMPOUND SUITABLE FOR MOCVD

(75) Inventors: Atsushi Itsuki, Omiya; Taiji Tachibana, Hyogo; Hiroto Uchida; Katsumi Ogi, both of Omiya, all of (JP)

(73) Assignee: Mitsubishi Materials Corporation, Tokyo (JP)

( * ) Notice: Subject to any disclaimer, the term of this patent is extended or adjusted under 35 U.S.C. 154(b) by 0 days.

(21) Appl. No.: 09/855,727

(22) Filed: May 16, 2001

Related U.S. Application Data (62) Division of application No. 09/231,300, filed on Jan. 15, 1999, now Pat. No. 6,280,518.

(30) Foreign Application Priority Data

| Feb. 9, 1998 | (JP) | ............................................ 10-027241 |
| Feb. 9, 1998 | (JP) | ............................................ 10-027243 |
| Mar. 11, 1998 | (JP) | ............................................ 10-059581 |

(51) Int. Cl.$^7$ .............................. C07F 7/28; C23L 16/40
(52) U.S. Cl. .................. 106/287.19; 501/134; 501/136; 501/137; 501/138; 427/255.32; 427/255.36
(58) Field of Search ...................... 106/287.19; 501/134, 501/137, 138, 136; 427/255.32, 255.36

(56) References Cited

U.S. PATENT DOCUMENTS 5,767,302 A    6/1998   Ogi et al.

FOREIGN PATENT DOCUMENTS

| JP | 5-271253 | 10/1993 |
| JP | 9-40683 | 2/1997 |
| JP | 10-72475 | 3/1998 |

OTHER PUBLICATIONS

Journal of the American Chemical Society, 90:21, (Oct. 9, 1968); pp. 5701–5706, "On the Question of Ring Currents in Metal Acetylacetonates, Electric Field Effects on the Proton Resonances of Cationic and Anionic β–Diketonate Complexes", R. Fay, et al.

Journal of the American Chemical Society, vol. 105, No. 8 (1983) no month provided, pp. 2118–2127, "Nuclear Magnetic Resonance Studies of Inversion and Diketonate R–Group Exchange in Dialkoxybis(β0diketonato)titanium(IV) Complexes. Evidence for a Twist Mechanism", R. Fay, et al.

J.C.S. Dalton, pp. 1128–1134, "A Comparative Dynamic Nuclear Magnetic Resonance Study of Degenerate Enationmerization and Dionate Site Exchange in Octahedral Diolatobis(pentane–2,4–dionato)titanium(IV) Complexes", N. Baggett, et al. No month proveded, No date provided.

Journal of the American Chemical Society, 97:20, (Oct. 1, 1975,)"Dynamic Nuclear Magnetic Resonance Studies of Inversion and Diketonate R–Group Exchange in Dialkoxybis(β–diketonato)titanium(IV) Complexes", R. Fay, et al.

*Primary Examiner*—David Brunsman
(74) *Attorney, Agent, or Firm*—Oblon, Spivak, McClelland, Maier & Neustadt, P.C.

(57) ABSTRACT

Bis(dipivaloylmethanato)diisobutoxytitanium or bis(dipivaloylmethanato)-di(2,2 -dimethyl-1-propoxytitanium per se, or as used as a raw material in a MOCVD process, as is or as a solution in an organic solvent, for example, tetrahydrofuran, produces a dielectric thin film of a fine texture having a film thickness which is proportional to the deposition time and the concentration of the solution.

13 Claims, 4 Drawing Sheets

ORGANIC TITANIUM COMPOUND SUITABLE FOR MOCVD

This application is a Division of application Ser. No. 09/231,300 filed on Jan. 15, 1999, now U.S. Pat. No. 6,280,518.

BACKGROUND OF THE INVENTION

1. Field of the Invention

The present invention relates to a novel organic titanium compound that is useful as a titanium source in the production of a metal oxide thin film containing titanium by a metal-organic chemical vapor deposition (MOCVD) process. The present invention also relates to a stock solution containing the compound for a MOCVD process, and a method for forming a titanate dielectric thin film using the stock solution. The metal oxide thin film containing titanium is useful as not only a dielectric thin film but also as a semiconductor thin film, an optical thin film, a surface reinforcing film, and a thin film catalyst.

2. Discussion of the Background

The rapid increase in integration density of DRAMs has required that compound oxide dielectric materials be used as capacitors having higher dielectric constants than those of conventional $SiO_2$ dielectric thin films, which have been used with great difficulty. Examples of compound oxide dielectric materials include titanium-containing compound oxides, such as, lead titanate (PT), lead zirconate titanate (PZT), lead lanthanum zirconate titanate (PLZT), strontium titanate (ST), barium titanate (BT), and barium strontium titanate (BST). Among them, BST is most preferable in view of dielectric characteristics.

Sol-gel processes have been vigorously studied for the production of compound oxide dielectric thin films, in which metal alkoxide solutions are applied onto substrates by spin coating methods. In the sol-gel processes, applied metal components are completely used as films without evaporation; hence the compositions of the films can be easily controlled. Capacitor electrodes for DRAMs, however, have larger steps that have complicated configurations with integration density. Thus, a uniform dielectric thin film is barely formed on an electrode substrate by a spin coat method.

For several years recently, deposition of dielectric thin-films by MOCVD processes has been actively studied in anticipation of a trend towards higher integration density of semiconductor devices, since the methods have superior step covering characteristics, that is, coating ability on complicated surfaces having steps. Organometallic compounds as raw materials generally used are organometallic complexes and metal alkoxides having β-diketone ligands such as dipivaloylmethane (DPM). Alkoxide or β-diketone complexes are used as sources of metals, such as Ti, Zr, and Ta, and β-diketone complexes are also used as sources of Sr and Ba.

In the MOCVD process, a metal source is evaporated by heat under a reduced pressure, and then the vapor is transferred into a deposition chamber and decomposed on a substrate to deposit the resulting metal oxide on the substrate. In the above-mentioned compound oxide thin film, at least two types of organometallic compounds must be used. Since these compounds have different vaporization characteristics in the MOCVD process, control of volumes of the compounds supplied to the deposition chamber is significantly important for the control of the film composition.

At the beginning of the formation of a dielectric thin film by a MOCVD process, organometallic compounds have been directly evaporated by heat and the formed vapor has been transferred into a deposition chamber. The organometallic compounds and particularly DPM complexes that have been recommended in the MOCVD process are unstable and barely vaporizable. As a result, vaporization will be inactivated in the operation or pyrolysis will occur prior to the vapor of the compounds reaching the deposition chamber. Thus, it is difficult to achieve stable transfer of the vapor of the compounds into the deposition chamber. Expensive raw materials should be disposed after one film deposition cycle. Furthermore, the film composition is controlled with difficulty, resulting in unstable supply of thin films having superior dielectric characteristics.

In order to solve such problems, a solution feeding method has been developed, in which a stock solution of organometallic compounds dissolved in an organic solvent is supplied into a vaporization chamber placed in front of a deposition chamber, and then the vapor in the vaporization chamber is fed to the deposition chamber for film deposition. Since DPM complexes are stable in solution, the stock solution can be repeatedly used. Furthermore, the heating temperature decreases due to vaporization to prevent pyrolysis of the compounds before they reach the deposition chamber. As a result, the film composition can be readily controlled.

Japanese Patent Laid-Open No. 5-271253 discloses bis(dipivaloylmethanato)-dialkoxy titanium complex [Ti(DPM)$_2$(OR)$_2$ wherein R is lower alkyl] as an organic titanium compound which is used as a raw material in a MOCVD process. Only bis(dipivaloylmethanato)-diisopropoxy titanium [Ti(DPM)$_2$(O-i-Pr)$_2$] is disclosed as a typical example when the R is isopropyl. Japanese Patent Laid-Open No. 9-40683 discloses bis(dipivaloylmethanato)-di-tert-butoxy titanium [Ti(DPM)$_2$(O-t-Bu)$_2$] as an organic titanium compound suitable for a solution feeding method.

In the solution feeding method, however, a low concentration solution must be used when the solubility of the organometallic compounds is low in the organic solvent; hence the deposition rate significantly decreases, resulting in inefficient film deposition. On the other hand, the use of a solution of a nearly saturated concentration causes precipitation of the compounds during the feeding of the stock solution due to evaporation of the solvent. As a result, the concentration of the stock solution varies, and the composition of the resulting film also varies. Accordingly, it is difficult to control the film composition. Some organometallic compounds are reactive with other organometallic compounds and/or the solvent, resulting in a decrease in vaporization of the compounds. As a result, it is difficult to control the film composition, and clogging will frequently occur due to the residue in the vaporization chamber and the coagulation in pipes and nozzles.

Requirements for the organometallic compounds are high solubility in an organic solvent, stable vaporization, and inertness to the other raw compounds and the solvent before the vaporization. Other important factors for the MOCVD process include high vaporization characteristics at a low temperature and high step covering characteristics over a wide temperature range from a low temperature to a high temperature.

In the formation of BST thin films, DPM complexes, i.e., Ba(DPM)$_2$ and Sr(DPM)$_2$ and their adducts are exclusively used as barium and strontium sources for the reason that any other suitable compounds are not found. As titanium sources, titanium alkoxide and titanium DPM complex are conventionally used, but these have insufficient film deposition characteristics. In the case of the formation of a BST film by a MOCVD process, titanium functions as nuclei of the film deposition. Thus, the deposition of barium and strontium is decelerated when the deposition of titanium is delayed; hence the titanium compound has significant effects on the deposition rate of the BST film.

For example, titanium alkoxides such as titanium isopropoxide among conventional titanium sources are reactive with Ba(DPM)$_2$ and Sr(DPM)$_2$, hence their vaporization characteristics significantly deteriorate. DPM complex of titanium, i.e., TiO(DPM)$_2$ is generally present as a dimer or a trimer, and it has inferior vaporization characteristics.

Use of titanium alkoxide DPM complexes is also known. Among such types of complexes which have been proposed, a complex having isopropyl groups as alkoxy groups, [Ti(DPM)$_2$(O-i-Pr)$_2$], has a low vaporization temperature; however, it can be easily polymerized, resulting in deterioration of evaporation characteristics and thus a significant decrease in the film deposition rate. Another complex having n-butoxy groups as alkoxy groups, [Ti(DPM)$_2$(O-n-Bu)$_2$] also has the same problem. Although a complex having t-butoxy groups as alkoxy groups. [Ti(DPM)$_2$(O-t-Bu)$_2$], shows low reactivity with Ba(DPM)$_2$ and Sr(DPM)$_2$ in the solution, it has low solubility in organic solvents. Thus, the film deposition rate of this compound is also low.

SUMMARY OF THE INVENTION

It is an object of the present invention to provide an organic titanium compound which has high solubility in organic solvents, shows stable vaporization at a low temperature, is stable in a vaporized state, and is capable of forming a dielectric thin film having a readily controlled composition with a significantly high deposition rate and superior step covering characteristics over a wide temperature range from a low temperature to a high temperature by either a solid supply method or a solution supply method, when the compound is used as a raw material in a MOCVD process.

The present inventors have discovered that titanium alkoxide DPM complexes wherein the alkoxy group is an isobutoxy or neopentyloxy (=2,2-dimethylpropoxy) group can solve the above-mentioned problems. The titanium compounds are novel titanium compounds represented by the general formula Ti(DPM)$_2$(OR)$_2$, wherein DPM represents dipivaloylmethanato and R represents a isobutyl or neopentyl group.

The present invention also provides a stock solution for MOCVD comprising a solution of such an organic titanium compound dissolved in an organic solvent, and a method for forming a titanate thin film by MOCVD comprising the use of the stock solution as a titanium source.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 7 includes electron microscopic photographs showing fine textures of BST thin films deposited using conventional organic titanium compounds as a titanium source; that is, FIG. 7(a) for Ti(DPM)$_2$(O-i-Pr)$_2$ and FIG. 7(b) for Ti(DPM)$_2$.

DETAILED DESCRIPTION OF THE INVENTION

Novel organic titanium compounds in accordance with the present invention represented by the general formula Ti(DPM)(OR)$_2$, wherein DPM and R are described above, include the following two compounds:

(1) bis(dipivaloylmethanato)-diisobutoxytitanium

(2) bis(dipivaloylmethanato)-di-(2,2-dimethyl-1-propoxytitanium)

Hereinafter, these compounds may be expressed by the following abbreviations:

Compound (1): Ti(DPM)$_2$(O-i-Bu)$_2$

Compound (2): Ti(DPM)$_2$(O-DMPr)$_2$ (DMPr= dimethylpropyl)

These two organic titanium compounds Ti(DPM)$_2$(O-i-Bu)$_2$ and Ti(DPM)$_2$(O-DMPr)2 are each a mixture of a cis-isomer and a trans-isomer that will be represented by the following structural formulae. Since the cis-isomer and the trans-isomer have very near boiling points and melting points, these are inseparable. Thus, bis (dipivaloylmethanato)-diisobutoxytitanium can be isolated as a mixture of the cis-and trans-isomers.

-continued

In the formulae A is H or CH₃. More specifically, A=H for the compound (1), i.e., bis(dipivaloylmethanato)-diisobutoxytitanium or Ti(DPM)₂(O-i-Bu)₂, and A=CH₃ for the compound (2), i.e., bis(dipivaloylmethanato)-di-(2,2-dimethyl-1-propoxytitanium) or Ti(DPM)₂(O-DMPr)₂.

The organic titanium compounds can be directly produced by a reaction of the corresponding tetraalkoxytitanium compounds represented by the general formula Ti(OR)₄, wherein R is the same as above [tetraisobutoxytitanium for the compound (1) or tetra-2,2-dimethyl-1-propoxy)titanium= tetra-neopentoxytitanium for the compound (2)] with dipivaloylmethane (=2,2,6,6-tetramethyl-3,5-heptanedione) in an adequate solvent. Since the tetraalkoxytitanium compounds as the starting materials, however, are not commercially available, the following process using commercially available products may be employed.

The starting material used is, for example, tetraisopropoxytitanium. The starting material is dissolved into an adequate solvent. Examples of preferred solvents include aromatic hydrocarbons, such as benzene, toluene, xylene, and mesitylene; and aliphatic hydrocarbons, such as pentane and hexane.

Alcohol represented by the general formula ROH wherein R is the same as above, i.e., 2-methyl-1-propanol (=isobutyl alcohol) for the compound (1) or 2,2-dimethyl-1-propanol (=neopentyl alcohol) for the compound (2), is added to the solution in an amount of two times by molar ratio that of the starting material. The solution is heated to near the boiling point or higher of the alcohol, i.e., isopropyl alcohol, which corresponds to the alkoxy group in the starting material, to form diisopropoxydiisobutoxytitanium or diisopropyldineopentyl-oxytitanium in which two isopropoxy groups among four groups in the starting material are replaced with RO groups. Although more isopropoxy groups may be replaced by increasing the volume of alcohol (ROH), such excessive replacement causes an increase in production cost since the reaction successfully proceeds by the replacement of the two groups.

The solution is cooled to room temperature, and then two times by molar ratio to the starting material of diplvaloylmethane is added. The isopropoxy groups having higher reactivity are predominantly released and dipivaloylmethane combines with titanium. Bis(dipivaloylmethanato)-diisobutoxytitanium or bis(dipivaloylmethanato)-di-(2,2-dimethyl-1-propoxy)titanium is thereby formed. The solution is concentrated to isolate the product from the solution as crystal. The remaining water and OH groups are removed from the product during the concentration process. In this method, a mixture composed of a major amount of cis-isomer and a minor amount of trans-isomer is generally obtained.

Removal of water contributes to an improvement in storage stability of the product. Sr(DPM)₂ and Ba(DPM)₂ as strontium and barium sources are highly reactive with OH groups, vaporization characteristics of the raw materials will decrease when such a reaction occurs. This causes some problems, that is, an increase in the residue in the vaporization chamber, an increase in clogging in pipes and nozzles, and difficult control of the film composition. The removal of the OH groups by the concentration can solve these problems in the BST film deposition.

The resulting crystal may be purified by recrystallization or the like, if necessary. It is preferable that the purified crystal of bis(dipivaloylmethanato)-diisobutoxytitanium or bis(dipivaloylmethanato)-di-(2,2-dimethyl-1-propoxy) titanium contain 0.1 percent by weight or less of OH groups and 5 ppm or less of residual chlorine.

Bis(dipivaloylmethanato)-diisobutoxytitanium or bis (dipivaloylmethanato)-di-(2,2-dimethyl-1-propoxy)titanium in accordance with the present invention is present as a monomer, hence it has high solubility in organic solvents, is steadily vaporized at low temperatures, and is stable in solution and vapor. Since the product is inert to strontium sources and barium sources, it can be used for the formation of MOCVD films by either a solid feeding method or a solution feeding method, and the film composition can be readily controlled. In the solution feeding method, a highly concentrated solution can be used and pyrolysis rapidly and completely proceeds as shown in the thermogravimetric curves in the Examples below. As a result, a significantly high film deposition rate can be achieved.

The resulting dielectric thin film has superior step covering characteristics over a wider temperature range from a low temperature to a high temperature. Since the organic titanium compound in accordance with the present invention has stable vaporization characteristics and stability after vaporization, the thickness of the dielectric thin film formed by the MOCVD process increases substantially in proportion to the deposition time. Since the compound has high solubility and stability as a solution in a solution feeding method, the concentration due to precipitation of raw materials does not occur. Thus, the thickness of the dielectric thin film increases substantially in proportion to the concentration of the solution. Accordingly, the film thickness can be readily controlled by the deposition time, and the concentration of the solution in the case of the solution feeding method.

Since the film deposition rate is high and is substantially proportional to the concentration, a dielectric thin film having a large thickness of several thousands of manometers can be formed by increasing the concentration of the solution in a short time, for example, five minutes. The thickness of the dielectric film reaches ten thousand manometers (=10 μm) for a deposition time of 20 minutes or more. Accordingly, a dielectric thin film having controlled thickness and composition can be formed for a significantly short deposition time compared with conventional processes.

The film deposition by MOCVD may be performed by any conventional process. For example, in a solid supplying method, vapor formed by heating of the raw compounds in a vaporization chamber is fed with a carrier gas into a deposition chamber.

In the solution feeding method, organometallic compounds as raw materials are used as a stock solution in an organic solvent. In this case, the stock solution is a solution bis(dipivaloylmethanato)-diisobutoxytitanium or bis (dipivaloylmethanato)-di-(2,2-dimethyl-1-propoxy)titanium as a titanium source in an organic solvent. For example, in the formation of a BST thin film, the stock solution may further contain a Sr compound and a Ba compound. Alternatively, a Sr compound and a Ba compound may be used as two different solutions.

When the different solutions are used, the organic solvents may be the same or different. When one stock solution of all of the raw compounds dissolved in an organic solvent is used, the concentration of each compound in the solution is determined so that a thin film having a predetermined composition is formed. The titanate complex in accordance with the present invention has low reactivity with the other raw compounds, for example, $Sr(DPM)_2$ and $Ba(DPM)_2$, for the dielectric thin film; hence the metallic ratio in the dielectric thin film is substantially the same as the metallic ratio in the raw compounds. As a result, the film composition can be easily controlled.

Any organic solvents can be used without restriction in the solution feeding method, and a preferred organic solvent is at least one selected from the group consisting of cyclic or acyclic alkanes, cyclic or acyclic monoethers and diethers, alkoxyalcohols, diols, esters, and substituted or unsubstituted pyridines.

Since alkanes have low reactivity and low azeotropic vapor pressure, $Sr(DPM)_2$ as an example can be dissolved as it is into an alkane solvent without coordination of the solvent. Accordingly, the solution can be steadily vaporized without pyrolysis of the organometallic compounds before the compounds reach the deposition chamber.

On the other hand, all of cyclic or acyclic monoethers and diethers, alkoxyalcohols, diols, esters, and substituted or unsubstituted pyridines are polar solvents. These polar solvent other than esters coordinate with the organometallic compounds by solvation to form complexes. Since esteric solvents have low polarity and high viscosity, the dissolved organometallic compounds are stable in the solution. Among these polar solvents, tetrahydrofuran (THF), one of cyclic monoethers, has high reactivity. Since the organic titanium compound in accordance with the present invention is stable, it can be dissolved into THF without deterioration of vaporization characteristics due to reaction with the solvent.

It is preferable that cyclic or acyclic alkane solvents have five to eight carbon atoms. Examples of the alkane solvents include linear alkanes, e.g., n-pentane, n-heptane, and n-octane; branched alkanes, e.g., isopentane and isooctane; and cycloalkanes, e.g., cyclopentane, cyclohexane, cycloheptane, and cyclooctane.

It is preferred that acyclic diethers be lower dimethoxyalkanes and diethoxyalkanes having 3 to 12 carbon atoms and more preferably no greater than 10 carbon atoms in view of the boiling point. Examples of acyclic diethers include dimethoxymethane, 1,1-dimethoxyethane, 1,2-dimethoxyethane, 1,1-diethoxyethane, 1,2-diethoxyethane, 3,4-dimethoxy-2,2-dimethylbutane, 3,4-dimethoxy-2,2-diethylbutane, 2,3-dimethoxy-1,1-dimethylpropane, 2,3dimethoxy-1,1-diethylpropane, 1,2-dimethoxyhexane, 1,2-diethoxyhexane, 1,2-dimethoxybutane, 1,2-diethoxybutane, 1,2-dimethoxypropane, and 1,2-diethoxypropane. A preferable cyclic diether is dioxane.

The acyclic monoethers are generally dialkylethers, and the two alkyl groups have preferably one to six carbon atoms. Although monoethers having two linear alkyl groups (a typical example is diethylether) can be used, monoethers having one or two branched alkyl groups are preferable. Examples of such monoethers include diisobutyl ether, diisopropyl ether, isobutyl methyl ether and isobutyl ethyl ether.

Examples of cyclic monoethers include unsubstituted tetrahydrofaran (THF), and lower-alkyl-substituted tetrahydrofurans. Preferable examples of lower-alkylsubstituted tetrahydrofuran include methyl- or dimethylsubstituted tetrahydrofurans, such as, 2-methyltetrahydrofuran (2-methylTHF), 3-methyltetrahydrofuran (3-methylTHF), and 2,5-dimethyltetrahydrofuran (2,5dimethylTHF).

Alkoxyalcohols have preferably 3 to 12, and more preferably no greater than 8 carbon atoms. Examples of such alkoxylalcohols include 1-ethoxy-2-propanol and 1-butoxy-2-propanol.

Diols have preferably two to four carbon atoms. Propylene glycol is more preferable.

Preferable esters are alkyl acetates and alkyl acetoacetates wherein the alkyl has one to five carbon atoms. Examples of such esters include methyl acetate, ethyl acetate, propyl acetate, isopropyl acetate, butyl acetate, isobutyl acetate, pentyl acetate, isopentyl acetate, methyl acetoacetate, and ethyl acetoacetate.

Among substituted or unsubstituted pyridines, pyridine and lower-alkyl-substituted pyridines are preferable. Examples of the lower-alkyl-substituted pyridines include 2,5-lutidine and 2,6-lutidine.

These solvents may be used alone or in combination. Examples of more preferable solvents include methyl- or dimethyl-substituted tetrahydrofurans, for example, 2-methylTHF, 3-methylTHF, and 2,5-dimethylTHF. A preferable mixed solvent is a combination of an alkane (=acyclic saturated hydrocarbon) being a nonpolar solvent with at least one polar solvent.

Although the stock solution can be directly evaporated from the solution vessel, it is preferable that the solution be fed into a heated vaporization chamber, instantaneously evaporated in the vaporization chamber, and then the vapor be fed to the deposition chamber. When different solutions of raw compounds are prepared, it is preferable that these solutions be fed into a mixing chamber provided in front of the vaporization chamber, and the solution mixture be fed into the vaporization chamber. The stock solutions may be fed by compressing them with an inert carrier gas, e.g., nitrogen, helium, or argon. The flow rate can be controlled by any flow rate controller.

The concentration of the stock solution is not limited. In the organic titanium compound in accordance with the present invention, the concentration is preferably in a range of 0.05 M to 3.0 M, and more preferably 0.1 M to 2.0 M. Since the organic titanium compound has high solubility, a highly concentrated solution of 1 M or more can be prepared, and thus a significantly high deposition rate can be achieved, as will be described below.

Preferable film deposition conditions include a substrate temperature in a range of 400 to 650° C., and a deposition pressure in a range of 5 to 20 Torr. The feeding rate of the stock solution is preferably in a range of 0.05 to 0.5 cc/min. Use of a carrier gas preferably performs the vaporization in either the solid feeding method or the solution feeding method. Examples of preferable carrier gases include inert gases, such as helium and argon. The flow rate of the carrier gas is preferably in a range of 300 to 700 ccm. A reactive gas, for example, oxygen or an oxygen-containing gas is supplied into the reaction chamber. The feeding rate when oxygen is used is preferably in a range of 500 to 2,000 ccm. The deposition time is determined so that a dielectric thin film having a predetermined thickness is formed. The deposition time is generally shorter than that of conventional processes, that is, less than one minute to several minutes. These conditions may be outside the above-described ranges in some cases.

The dielectric thin film produced by a MOCVD process using an organic titanium compound in accordance with the present invention is useful as a capacitor of a DRAM. When the organic titanium compound in accordance with the present invention is used, a dielectric thin film having superior step covering characteristics can be produced for a short deposition time over a wide temperature range and a wide range of concentration.

Figure 1:
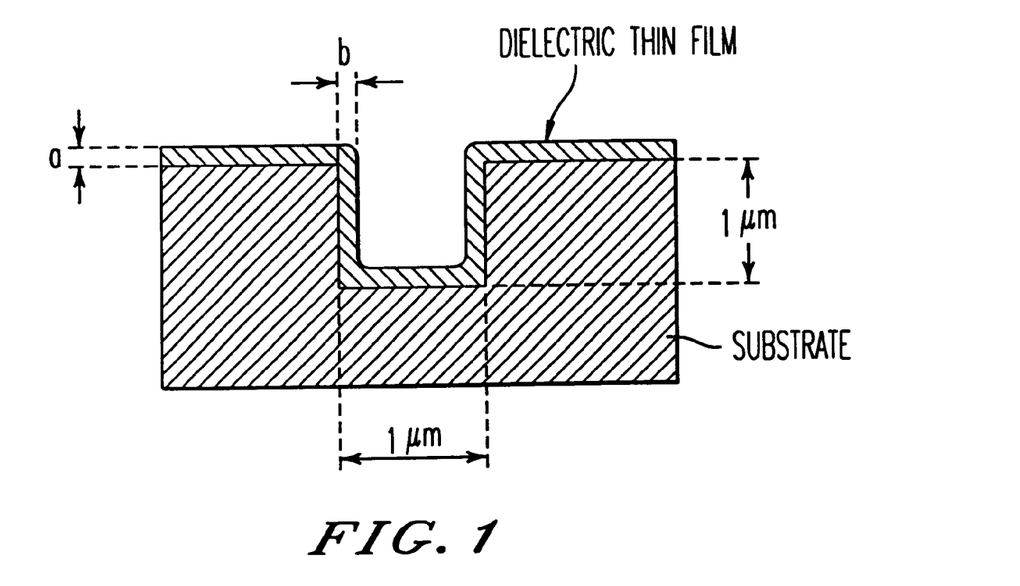
FIG. 1 is a schematic view of a method for evaluating the step covering characteristics.

As shown in FIG. 1, when a thin film is deposited on a substrate having an indented section with a volume of 1 $\mu m^3$ (that is, each of the length, width and depth is 1 $\mu m$), the step covering characteristics in the present invention is defined as the ratio b/a of the film thickness b in the indented section to the film thickness a on the flat portion of the substrate. A ratio near to 1 means superior step covering characteristics. Thus, the ideal b/a value is 1. In such a case, the thickness of the thin film is preferably in a range of 15 to 30 mm.

As described above, the dielectric thin film formed of the organic titanium compound in accordance with the present invention is useful as a capacitor of a DRAM. The dielectric thin film also can be used in piezoelectric vibrators and infrared sensors as dielectric filters. Furthermore, the organic titanium compound in accordance with the present invention can be used for the formation of semiconductor films, optical thin films, surface-reinforcing films, and thin-film catalysts.

Having generally described this invention, a futher understanding can be obtained by reference to certain specific examples which are provided herein for purposes of illustration only and are not intended to be limiting unless otherwise specified.

EXAMPLE 1

Into 500 liters of benzene, 290 g (1 mol) of tetraisopropoxytitaniuin was dissolved, 144 g (2 mol) of 2-methyl-1-propanol was added to the solution, and then the solution was refluxed for 2 hours. The solution after the reaction was cooled to room temperature, 368.5 g (2 mol) of dipivaloylmethane was added, and then immediately the solution was concentrated by heat. The solution was cooled, and the precipitated crystal was separated by filtration. A powdered bis(dipivaloylmethanato)-diisobutoxytitanium (150 g, the yield: 60%) was prepared. The melting point was 120 to 130° C., and the decomposition temperature was 300 to 340° C.

The product was identified by $^1$H-NMR, IR, spectrometry, mass spectrometry, and elemental analysis.

$^1$H-NMR ($C_6D_6$+THF) δ(ppm): 1.6[C(CH$_3$)$_3$] 1.8(CH$_3$), 3.4(CH$_2$), 4.2 (CH), 5.8 (CH);

IR: 1,730, 1,725, 1,259, 1,300, 3,100, 1,330, 1,590, 1,600, 1,030, 670, 900, 110, 1,470,

Mass spectra (m/z): 31, 161, 342, 490, 538, 561;

Elemental analysis: $C_{30}H_{56}O_6Ti$ (Calculated) C:64.22, H:10.06, 0:17.15, Ti:8.540

(Observed) C:64.25, H:10.07, O:17.12, Ti:8.542

The mass spectrometric data shows that the organic titanium compound in accordance with the present invention is present as a monomer.

Figure 2:
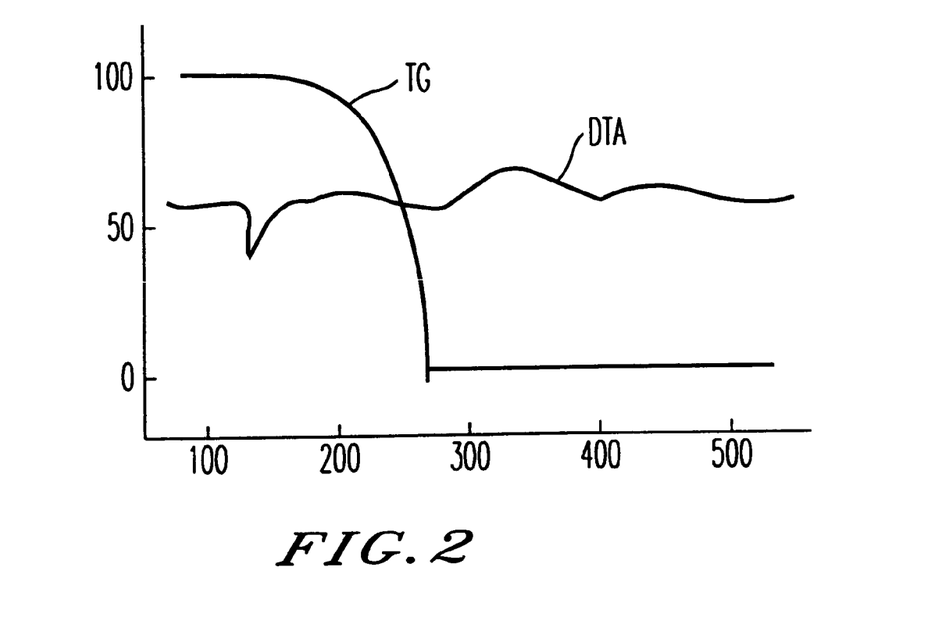
FIG. 2 is a TG-DTA thermogram of bis (dipivaloylmethanato)-diisobutoxytitanium in accordance with the present invention.

FIG. 2 is a TG-DTA thermogram of thermal gravimetry (TG) and differential thermal analysis (DTA) of the compound at a heating rate of 10° C./min in an argon stream.

EXAMPLE 2

White powdered bis(dipivaloylmethanato)-di-(2,2-dimethyl-1-propoxy)titanium (yield: approximately 60%) was prepared as in Example 1, but 176 g (2 mol) of 2,2-dimethyl-1-propanol was used instead of 2-methyl-1-propanol. Sublimed (180° C./2 Torr), decomposition temperature: 310 to 350° C.

The product was identified by $^1$H-NMR, IR spectrometry, mass spectrometry, and elemental analysis.

$^1$H-NMR ($C_6D_6$+THF) δ(ppm): 1.4[C(CH$_3$)$_3$], 1.75 (CH$_3$), 3.4(CH$_2$), 5.8 (CH);

IR: 1,730, 1,725, 1,259, 1,300, 3,100, 3,150, 1,330, 1,590, 1,600, 1,030, 670, 110, 1,470;

Elemental analysis: $C_{32}H_{60}O_6Ti$ (Calculated) C:65.1, H:10.1, O:16.2, Ti:7.97

(Observed) C:64.9, H:10.4, O:16.5, Ti:8.00

Figure 3:
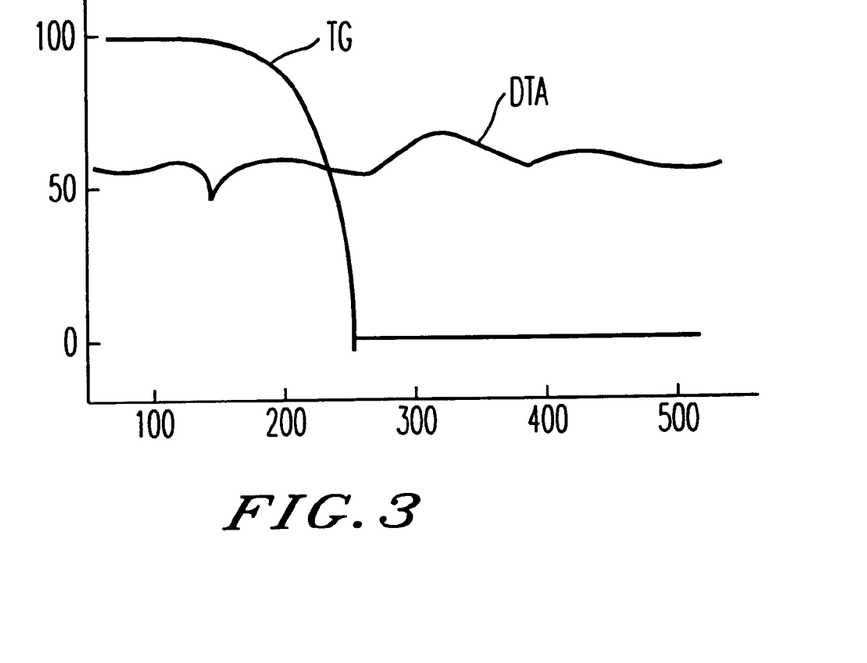
FIG. 3 is a TG-DTA thermogram of bis (dipivaloylmethanato)-di(2,2-dimethyl-1-propoxytitanium in accordance with the present invention.

FIG. 3 is a TG-DTA thermogram of thermal gravimetry (TG) and differential thermal analysis (DTA) of the compound at a heating rate of 10° C./min in an argon stream. The endothermic peak due to melting is smaller than that of the compound in Example 1, since the compound is sublimed.

Figure 4:
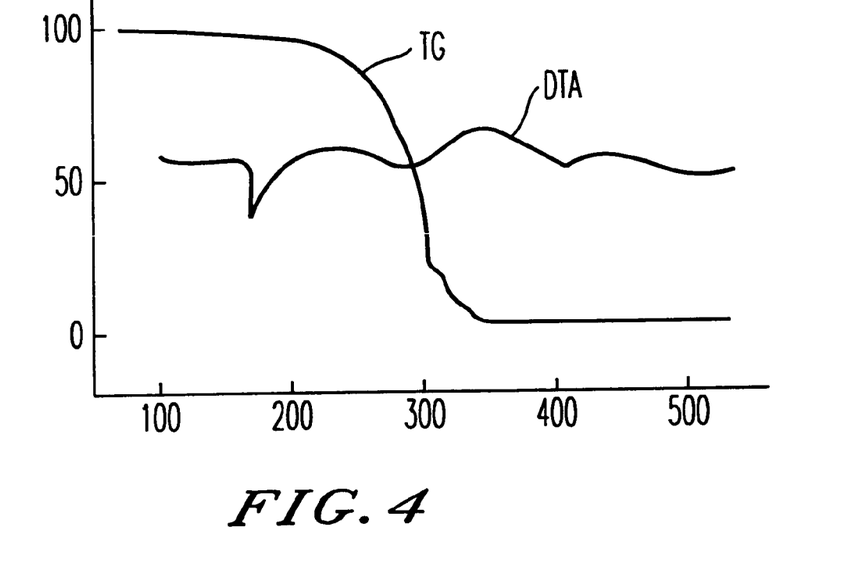
FIG. 4 is a TG-DTA thermogram of known bis (dipivaloylmethanato)-diisopropoxytitanium.

FIG. 4 is a TG-DTA thermogram for comparison of thermal gravimetry (TG) and differential thermal analysis (DTA) of bis-(dipivaloylmethanato)-diisopropoxytitanium, that is, a conventional compound having an isopropyl group as an alkoxy group instead of the isobutyl group.

By comparing FIGS. 2 and 3 (compounds in accordance with the present invention) with FIG. 4 (a conventional compound), bis(dipivaloylmethanato)-diisobutoxytitanium and bis(dipivaloylmethanato)-di-(2,2-dimethyl-1-propoxytitanium) in accordance with the present invention have lower melting points than that of known bis (dipivaloylmethanato)-diisopropoxytitanium. Furthermore, thermal decomposition rapidly proceeds and the decomposition is completed at approximately 280° C. or less. In contrast. the conventional compound is gradually decomposed, and not completely decomposed at 350° C. since the decomposition is delayed at the final stage.

EXAMPLE 3

Using the organic titanium compound [Ti(DPM)$_2$ (O-i-Bu)$_2$] prepared in Example 1, the organic titanium compound [Ti(DPM)$_2$(O-DMPr)$_2$] prepared in Example 2, and the conventional isopropoxy compound [Ti(DPM)$_2$(O-i-Pr)$_2$] as Ti sources, TiO$_2$ thin films were formed by a solid feeding method and a solution feeding method. An SiO$_2$ substrate was used. An indented portion with a width of 1 $\mu$m, a length of 1 $\mu$m, and a depth of 1 $\mu$m (1 $\mu m^3$) had been formed on the front surface of the substrate in order to evaluate step covering characteristics.

The deposition conditions were as follows:
Solution Feeding Method
  Solvent: THF
  Substrate temperature: 450° C.
  Deposition time: 5 to 30 minutes
  Deposition pressure: 10 Torr
  Feeding rate of solution: 0.1 cc/min
  Concentration of raw material: 0.1 to 2.0 M
  Reactive gas: oxygen (1,000 ccm)
  Vaporization temperature of raw material: 120° C.
  Carrier gas: helium (500 ccm)
Solid Feeding Method
  Substrate temperature: 450° C.
  Deposition time: 5 to 30 minutes
  Deposition pressure: 10 Torr
  Concentration of raw material: 0.1 to 2.0 M
  Reactive gas: oxygen (1,000 ccm)

Vaporization temperature of raw material: 120° C.

Carrier gas: helium (500 ccm)

In the solution feeding method, these titanium compounds were dissolved into THF to prepare three 0.1-M, 1.0-M and 2.0-M stock solutions. Each of the stock solutions was fed into a vaporization chamber heated to the vaporization temperature while controlling feeding rate, and the resultant vapor was fed into a deposition chamber with the carrier gas to form a $TiO_2$ thin film onto a substrate heated to the above-mentioned temperature in the deposition chamber.

In the solid feeding method, each raw organic titanium compound was vaporized at a vaporization temperature while flowing the carrier gas, and the resultant vapor was fed into a deposition chamber to form a $TiO_2$ thin film onto a substrate heated to the above-mentioned temperature in the deposition chamber.

The deposition time was changed from 5 minutes to 30 minutes by 5 minutes. The thickness of the BST thin film formed on the substrate was measured using a cross-sectional scanning electron microscopic (SEM) photograph.

Using a solution having a low concentration of 0.05 M, a thin film was deposited for a reduced deposition time, so that the thickness was approximately 20 nm. The thicknesses of the $TiO_2$ thin film at plural points in the indented section and the periphery (the flat portion of the substrate) of the indented section with a volume of 1 $\mu m^3$ were measured using a cross-sectional SEM photograph, and were averaged to determine the thickness a of the periphery and the thickness b of the indented section. The results of the ratio b/a as a measure of step covering characteristics are shown in Table 1.

MOCVD process using bis(dipivaloylmethanato) diisobutoxytitanium or bis(dipivaloylmethanato)-di-(2,2-dimethyl-1-propoxy)titanium in accordance with the present invention as a Ti source. The deposition rate by a solid feeding method is higher than that by a solution feeding method. The thickness of the deposited film increases substantially in proportion to the deposition time in both solution and solid feeding methods. In the solution feeding method, the thickness of the deposited film also increases substantially in proportion to the concentration of the solution. Thus, when the concentration of the solution in the solution feeding method is increased by 2.0 m, the film thickness reaches approximately 20 times or more that by the solid feeding method, or the thickness is higher than 10,000 nm (10 $\mu$m) for a deposition time of 30 minutes.

Since the film thickness is substantially proportional to the deposition time and the concentration of the solution in the solution feeding method, the film thickness can be easily controlled. Since the ratio showing step covering characteristics is 0.8 or higher, and near to 1, a thin film having a substantially uniform thickness can be deposited on the substrate having an uneven surface.

When films were similarly deposited at a higher substrate temperature of 600 to 650° C., the thicknesses were approximately 10 times those shown in Table 1, and the step covering ratio was 0.8 or higher and the same level as that shown in Table 1. Accordingly, superior step covering characteristics were achieved at any temperature from a low temperature to a high temperature.

In contrast, when known bis(dipivaloylmethanato) diisopropoxy titanium was used as a Ti source the film thickness was significantly small at all deposition times compared to that of the compounds in accordance with the present invention. Furthermore, the thickness is not propor-

TABLE 1

Titanium source: Ti(DPM)$_2$(O-i-Bu)$_2$ (this invention)

| Feeding method | Concentration of solution (M) | TiO$_2$ film thickness at different deposition time (nm) | | | | | | Step covering ratio (b/a) |
|---|---|---|---|---|---|---|---|---|
| | | 5 min | 10 min | 15 min | 20 min | 25 min | 30 min | |
| Solid | — | 150 | 300 | 500 | 600 | 700 | 800 | ~0.9 |
| Solution | 0.1 | 180 | 380 | 500 | 700 | 1,000 | 1,100 | ~0.9 |
| | 1.0 | 1,500 | 2,800 | 4,500 | 5,800 | 7,200 | 8,800 | ~0.8 |
| | 2.0 | 3,000 | 6,000 | 8,500 | 12,500 | 15,000 | 17,500 | ~0.9 |

Titanium source: Ti(DPM)$_2$(O-i-DMPr)$_2$ (this invention)

| Feeding method | Concentration of solution (M) | TiO$_2$ film thickness at different deposition time (nm) | | | | | | Step covering ratio (b/a) |
|---|---|---|---|---|---|---|---|---|
| | | 5 min | 10 min | 15 min | 20 min | 25 min | 30 min | |
| Solid | — | 135 | 250 | 400 | 550 | 680 | 800 | ~0.9 |
| Solution | 0.1 | 150 | 300 | 480 | 650 | 730 | 900 | ~0.9 |
| | 1.0 | 1,200 | 2,800 | 3,400 | 4,500 | 6,100 | 7,100 | ~0.8 |
| | 2.0 | 2,500 | 4,800 | 7,300 | 10,100 | 12,100 | 14,800 | ~0.9 |

Titanium source: Ti(DPM)$_2$(O-i-Bu)$_2$ (conventional)

| Feeding method | Concentration of solution (M) | TiO$_2$ film thickness at different deposition time (nm) | | | | | | Step covering ratio (b/a) |
|---|---|---|---|---|---|---|---|---|
| | | 5 min | 10 min | 15 min | 20 min | 25 min | 30 min | |
| Solid | — | 30 | 40 | 20 | 25 | 10 | 5 | ~0.2 |
| Solution | 0.1 | 50 | 100 | 70 | 60 | 20 | 10 | ~0.3 |
| | 1.0 | 20 | 30 | 10 | 5 | 5 | 3 | ~0.2 |
| | 2.0 | 5 | 15 | 38 | 20 | 8 | 1 | ~0.9 |

Table 1 shows that thin films can be formed at high deposition rates by either the solid or liquid method in a tional to the deposition time or concentration of the solution (in the solution feeding method). In detail, the thickness reaches a maximum at 10 to 15 minutes, and decreases at a longer deposition time. In the solution feeding method, the thickness decreases as the concentration of the solution increases, in contrast with the compounds in accordance with the present invention.

For example, a large thickness of 10,000 nm or more is achieved for a concentration of the solution of 2.0 M and a deposition time of 30 minutes when using a compound in accordance with the present invention, whereas a significantly small thickness of 1 nm is achieved for the same-conditions using the conventional compound.

Furthermore, the step-covering ratio is in a range of 0.1 to 0.3 and the thickness of the film formed in the indented section is 0.1 to 0.3 times that on the substrate surface.

The reason that the thickness is significantly small in the conventional compound seems to be insufficient evaporation due to a high vaporization temperature of the compound and low stability of the vapor (high reactivity) causing polymerization. The reason that the thickness decreases when the concentration of the solution is high and when the deposition time is longer than a predetermined time seems to be polymerization due to decreased molecular stability under such conditions. Since the titanium compound in accordance with row the present invention has a low vaporization temperature and high stability, hence it can be present as a monomer. Furthermore, it has high stability in vapor, is rapidly vaporized and, has high solubility, hence the film deposition rate is high, and the film thickness increases substantially in proportion to the deposition time and the concentration of the solution.

When bis-(dipivaloylmethanato)-di-n-butoxytitanium is used as another conventional compound instead of bis (dipivaloylmethanato)-diisopropoxytitanium, similar results to those of the conventional compound shown in Table 1 are obtained.

EXAMPLE 4

$TiO_2$ films were formed by a liquid feeding method as in Example 3 using the organic titanium compound [Ti(DPM)$_2$(O-i-Bu)$_2$] prepared in Example 1 in accordance with the present invention or the organic titanium compound [Ti(DPM)$_2$(O-DMPr)$_2$] prepared in Example 2 in accordance with the present invention as a Ti source, and using 2,5-dimethyltetrahydrofuran (2,5-DMeTHF), 2-methyltetrahydrofuran (2-MeTHF) or diisobutylether (DIBE) as a solvent in place of THF. The results of the $TiO_2$ film thickness and the step covering ratio are shown in Table 2 for Ti(DPM)$_2$(O-i-Bu)$_2$ and Table 3 for Ti(DPM)$_2$(O-DMPr)$_2$.

TABLE 2

Titanium source: Ti(DPM)$_2$(O-i-Bu)$_2$ (liquid feeding method)

| Solvent | Concentration of solution (M) | TiO$_2$ film thickness at different deposition time (nm) | | | | | | Step covering ratio (b/a) |
|---|---|---|---|---|---|---|---|---|
| | | 5 min | 10 min | 15 min | 20 min | 25 min | 30 min | |
| 2,5-DMeTHF | 0.1 | 200 | 400 | 510 | 680 | 980 | 1,200 | ~0.9 |
| | 1.0 | 1,800 | 3,000 | 4,400 | 5,700 | 7,300 | 9,000 | ~0.9 |
| | 2.0 | 2,900 | 5,800 | 8,800 | 12,550 | 14,900 | 18,000 | ~0.9 |
| 2-Me | 0.1 | 150 | 400 | 510 | 700 | 990 | 1,200 | ~0.9 |
| | 1.0 | 1,510 | 3,000 | 4,800 | 6,000 | 7,300 | 9,000 | ~0.9 |
| | 2.0 | 3,200 | 6,100 | 8,300 | 12,600 | 14,900 | 18,000 | ~0.9 |
| DIBE | 0.1 | 200 | 400 | 510 | 680 | 1,190 | 1,200 | ~0.9 |
| | 1.0 | 1,800 | 3,000 | 4,800 | 6,100 | 7,300 | 9,000 | ~0.9 |
| | 2.0 | 3,200 | 6,100 | 8,800 | 12,400 | 14,900 | 18,000 | ~0.9 |

2,5-DMeTHF = 2,5-dimethyltetrahydrofuran
2-MeTHF = 2-methyltetrahydrofuran
DIBE = diisobutylether

TABLE 3

Titanium source: Ti(DPM)$_2$(O-i-DMPr)$_2$ (liquid feeding method)

| Solvent | Concentration of solution (M) | TiO$_2$ film thickness at different deposition time (nm) | | | | | | Step covering ratio (b/a) |
|---|---|---|---|---|---|---|---|---|
| | | 5 min | 10 min | 15 min | 20 min | 25 min | 30 min | |
| 2,5-DMeTHF | 0.1 | 200 | 280 | 450 | 680 | 750 | 1,000 | ~0.9 |
| | 1.0 | 1,100 | 3,000 | 3,500 | 4,800 | 6,200 | 7,000 | ~0.9 |
| | 2.0 | 2,800 | 4,900 | 7,200 | 10,550 | 12,200 | 15,000 | ~0.9 |
| 2-MeTHF | 0.1 | 200 | 340 | 480 | 680 | 730 | 920 | ~0.9 |
| | 1.0 | 1,120 | 2,900 | 3,500 | 4,600 | 6,000 | 7,000 | ~0.9 |
| | 2.0 | 2,510 | 4,900 | 7,200 | 10,120 | 12,200 | 15,000 | ~0.9 |
| DIBE | 0.1 | 180 | 320 | 500 | 660 | 750 | 1,010 | ~0.9 |
| | 1.0 | 1,100 | 3,000 | 3,500 | 4,600 | 6,200 | 7,200 | ~0.9 |
| | 2.0 | 2,800 | 4,900 | 7,300 | 10,110 | 12,120 | 15,000 | ~0.9 |

2,5-DMeTHF = 2,5-dimethyltetrahydrofuran
2-MeTHF = 2-methyltetrahydrofuran
DIBE = diisobutylether The solvents other than THF shown in Tables 2 and 3 also enables the rapid formation of $TiO_2$ films by a liquid feeding MOCVD process using the organic titanium compounds in accordance with the present invention, wherein the thickness is substantially proportional to the deposition time and the concentration of the solution. The step-covering ratio is 0.9 or more which is higher than that when THF is used as a solvent.

Substantially the same results were obtained when 3-methyltetrahydrofuran was used instead of 2-methyltetrahydrofuran (2-MeTHF).

EXAMPLE 5

BST films were formed by a liquid feeding method using the organic titanium compound [Ti(DPM)$_2$(O-i-Bu)$_2$] prepared in Example 1 in accordance with the present invention or the organic titanium compound [Ti(DPM)$_2$(O-DMPr)$_2$] prepared in Example 2 in accordance with the present invention as a Ti source. Ba(DPM)$_2$ and Sr(DPM)$_2$ were used as a Ba source and a Sr source, respectively.

These metal sources were dissolved in different solvents to prepare stock solutions having concentrations of 0.1 to 0.2 M. The stock solutions were fed into a mixing chamber while controlling the flow rates so that the these metals satisfy the atomic ratio Ba:Sr:Ti=0.5:0.5:1, and the solution mixture was vaporized in a vaporization chamber. The vapor was fed into a deposition chamber, and BST thin films were on a $SiO_2$ substrates with Pt/It electrodes formed thereon by sputtering (Pt/Ti/SiO$_2$ substrate) under the following conditions:

Substrate: Pt/Ti/SiO$_2$

Substrate temperature: 400 to 650° C.

Deposition pressure: 10 Torr

Feeding rate of solution: 0.05 cc/min

Concentration of raw material: 0.1 to 0.2 M

Reactive gas: oxygen (1,000 ccm)

Vaporization temperature of raw material: 200 to 250° C.

Carrier gas: helium (500 ccm)

Deposition time: 20 minutes

Experiments on film deposition were performed at different substrate temperatures and using different solvents. The atomic ratios of metals in the resulting thin films were determined by fluorescent x-ray analysis. The results of the atomic ratio, Ti/(Ba+Sr), are shown in Table 4 for Ti(DPM)$_2$(O-i-Bu)$_2$ and Table 5 for Ti(DPM)$_2$(O-DMPr)$_2$. Since the metal source solutions were fed so as to satisfy the atomic ratio, Ba:Sr:Ti=0.5:0.5:1, the resulting film should have a composition of Ba$_{0.5}$Sr$_{0.5}$TiO$_3$ and thus an atomic ratio of 1/1 in an ideal state. For example, when the Ti/(Ba+Sr) atomic ratio is 0.1/0.3, this value means that the film contains large amounts of inclusions such as carbon.

For comparison, BST films were also formed using known TiO(DPM)$_2$ or TiO(DPM)$_2$(O-i-Pr)$_2$ as a titanium source. The results are shown in Table 6.

TABLE 4

Raw materials: Ba(DPM)$_2$ + Sr(DPM)$_2$ + Ti(DPM)$_2$(O-i-Bu)$_2$
(Examples)

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|
| THF | 400 | 1.2/1.1 | DMP | 400 | 1.0/1.1 |
|  | 450 | 1.1/1.0 |  | 450 | 1.1/1.0 |
|  | 500 | 1.1/1.0 |  | 500 | 1.0/1.0 |
|  | 550 | 1.1/1.1 |  | 550 | 1.2/1.1 |
|  | 600 | 1.0/1.1 |  | 600 | 1.1/1.2 |
|  | 650 | 1.1/1.1 |  | 650 | 1.3/1.0 |
| Pyridine | 400 | 1.0/1.1 | Lutidine | 400 | 1.0/1.1 |
|  | 450 | 1.1/1.2 |  | 450 | 1.0/1.0 |
|  | 500 | 1.0/1.1 |  | 500 | 1.1/1.2 |
|  | 550 | 1.0/1.2 |  | 550 | 1.0/1.1 |
|  | 600 | 1.0/1.0 |  | 600 | 1.1/1.1 |
|  | 650 | 1.0/1.1 |  | 650 | 1.0/1.0 |
| Isooctane | 400 | 1.0/1.1 | Butyl acetate | 400 | 1.0/1.1 |
|  | 450 | 1.0/1.2 |  | 450 | 1.1/1.1 |
|  | 500 | 1.2/1.1 |  | 500 | 1.0/1.0 |
|  | 550 | 1.0/1.2 |  | 550 | 1.1/1.0 |
|  | 600 | 1.0/1.0 |  | 600 | 1.0/1.1 |
|  | 650 | 1.0/1.1 |  | 650 | 1.0/1.1 |
| Octane | 400 | 1.0/1.1 | Cyclohexane | 400 | 1.0/1.1 |
|  | 450 | 1.0/1.0 |  | 450 | 1.1/1.1 |
|  | 500 | 1.0/1.0 |  | 500 | 1.0/1.0 |
|  | 550 | 1.2/1.1 |  | 550 | 1.0/1.0 |
|  | 600 | 1.0/0.9 |  | 600 | 1.0/1.1 |
|  | 650 | 1.1/1.0 |  | 650 | 1.0/1.0 |
| DMM | 400 | 1.0/1.1 | 2MeTHF | 400 | 1.0/1.1 |
|  | 450 | 1.1/1.0 |  | 450 | 1.0/1.0 |
|  | 500 | 1.2/1.2 |  | 500 | 1.1/1.1 |
|  | 550 | 1.0/1.0 |  | 550 | 1.0/1.1 |
|  | 600 | 1.1/1.0 | 600 | 1.1/1.0 |  |
|  | 650 | 1.1/1.0 |  | 650 | 1.0/1.0 |
| Hexane | 400 | 1.0/1.1 | Methyl acetate | 400 | 1.0/1.0 |
|  | 450 | 1.0/1.0 |  | 450 | 1.0/1.0 |
|  | 500 | 1.1/1.2 |  | 500 | 1.1/1.0 |
|  | 550 | 1.0/1.1 |  | 550 | 1.0/1.0 |
|  | 600 | 1.1/1.1 |  | 600 | 1.1/1.1 |

TABLE 4-continued

Raw materials: Ba(DPM)$_2$ + Sr(DPM)$_2$ + Ti(DPM)$_2$(O-i-Bu)$_2$
(Examples)

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|
|  | 650 | 1.2/1.0 |  | 650 | 1.2/1.0 |
| Dioxane | 400 | 1.0/1.0 | Isobutyl | 400 | 0.9/0.9 |
|  | 450 | 1.0/1.0 | acetate | 450 | 1.0/1.0 |
|  | 500 | 1.1/1.2 |  | 500 | 1.0/1.0 |
|  | 550 | 1.1/1.0 |  | 550 | 1.0/1.1 |
|  | 600 | 1.2/1.1 |  | 600 | 1.1/1.1 |
|  | 650 | 1.1/1.0 |  | 650 | 1.0/1.0 |
| Diisobutyl | 400 | 1.0/1.0 | Methyl | 400 | 1.0/1.1 |
| ether | 450 | 1.0/0.9 | aceto- | 450 | 1.1/1.1 |
|  | 500 | 1.0/1.2 | acetate | 500 | 1.0/1.0 |
|  | 550 | 1.1/1.0 |  | 550 | 1.0,1.0 |
|  | 600 | 1.1/1.0 |  | 600 | 1.0/1.1 |
|  | 650 | 0.9/1.0 |  | 650 | 1.0/1.0 |
| 2,5-DMeTHF | 400 | 1.0/1.0 | 1:1 | 400 | 1.0/1.1 |
|  | 450 | 1.0/1.0 | mixture | 450 | 1.1/1.0 |
|  | 500 | 1.1/1.1 | of | 500 | 1.1/1.0 |
|  | 550 | 1.0/1.0 | 2MeTHF | 550 | 1.1/1.1 |
|  | 600 | 1.1/1.0 | and 2,5- | 600 | 1.0/1.0 |
|  | 650 | 1.0/1.0 | DMeTHF | 650 | 1.1/1.0 |
| Ethyl | 400 | 1.0/1.1 | Isopropyl | 400 | 1.0/1.1 |
| acetate | 450 | 1.1/1.0 | acetate | 450 | 1.1/1.0 |
|  | 500 | 1.0/1.0 |  | 500 | 1.0/1.1 |
|  | 550 | 1.0/1.1 |  | 550 | 1.0/1.2 |
|  | 600 | 1.1/1.2 |  | 600 | 1.0/1.0 |
|  | 650 | 1.0/1.0 |  | 650 | 1.0/1.1 |
| Pentyl | 400 | 1.0/1.1 | Isopentyl | 400 | 1.0/1.0 |
| acetate | 450 | 1.1/1.0 | acetate | 450 | 1.1/1.1 |
|  | 500 | 1.1/1.2 |  | 500 | 1.0/1.0 |
|  | 550 | 1.0/1.0 |  | 550 | 1.1/1.0 |
|  | 600 | 1.1/1.0 |  | 600 | 1.0/1.1 |
|  | 650 | 1.1/1.0 |  | 650 | 1.2/1.0 |
| Ethyl | 400 | 1.0/1.1 |  |  |  |
| aceto- | 450 | 1.0/1.2 |  |  |  |
| acetate | 500 | 1.1/1.1 |  |  |  |
|  | 550 | 1.0/0.9 |  |  |  |
|  | 600 | 1.0/1.0 |  |  |  |
|  | 650 | 1.0/1.0 |  |  |  |

THF = tetrahydrofuran, DMP = dimethoxypropane
DMM = dimethoxymethane, 2MeTHF = 2-methyltetrahydrofuran
2,5-DMeTHF = 2,5-dimethyltetrahydrofuran

TABLE 5

Raw materials: Ba(DPM)$_2$ + Sr(DPM)$_2$ + Ti(DPM)$_2$(O-i-DMPr)$_2$
(Examples)

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|
| THF | 400 | 1.0/1.0 | DMP | 400 | 1.1/1.0 |
|  | 450 | 1.1/1.1 |  | 450 | 1.0/1.1 |
|  | 500 | 1.0/1.1 |  | 500 | 1.1/1.0 |
|  | 550 | 1.2/1.0 |  | 550 | 1.0/1.0 |
|  | 600 | 1.1/1.2 |  | 600 | 1.1/1.2 |
|  | 650 | 1.0/1.0 |  | 650 | 1.1/1.0 |
| Pyridine | 400 | 1.0/1.0 | Lutidine | 400 | 1.0/1.0 |
|  | 450 | 1.1/1.1 |  | 450 | 0.9/0.9 |
|  | 500 | 1.0/1.1 |  | 500 | 1.1/1.2 |
|  | 550 | 1.0/1.2 |  | 550 | 0.9/1.0 |
|  | 600 | 1.0/1.0 |  | 600 | 1.1/1.1 |
|  | 650 | 1.0/1.1 |  | 650 | 1.1/1.0 |
| Isooctane | 400 | 0.9/0.9 | Butyl | 400 | 1.0/1.0 |
|  | 450 | 1.0/1.2 | acetate | 450 | 1.1/1.1 |
|  | 500 | 1.0/1.0 |  | 500 | 1.2/1.1 |
|  | 550 | 1.0/1.0 |  | 550 | 1.0/1.1 |
|  | 600 | 1.0/1.0 |  | 600 | 1.2/1.0 |
|  | 650 | 0.9/0.8 |  | 650 | 1.1/1.1 |

TABLE 5-continued

Raw materials: Ba(DPM)₂ + Sr(DPM)₂ + Ti(DPM)₂(O-i-DMPr)₂ (Examples)

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|
| Octane | 400 | 1.0/1.0 | Cyclo- | 400 | 1.0/1.0 |
|  | 450 | 1.0/1.1 | hexane | 450 | 1.1/1.1 |
|  | 500 | 1.0/1.0 |  | 500 | 1.1/1.1 |
|  | 550 | 1.0/1.1 |  | 550 | 1.0/1.0 |
|  | 600 | 1.1/1.2 |  | 600 | 1.2/1.1 |
|  | 650 | 1.0/1.0 |  | 650 | 1.1/1.0 |
| DMM | 400 | 1.1/1.0 | 2MeTHF | 400 | 1.0/1.0 |
|  | 450 | 1.0/1.1 |  | 450 | 1.0/1.0 |
|  | 500 | 1.2/1.1 |  | 500 | 1.1/1.1 |
|  | 550 | 1.1/1.0 |  | 550 | 1.0/1.1 |
|  | 600 | 1.2/1.2 |  | 600 | 1.1/1.0 |
|  | 650 | 1.2/1.2 |  | 650 | 1.1/1.0 |
| Hexane | 400 | 1.0/1.1 | Methyl | 400 | 1.0/1.1 |
|  | 450 | 1.0/1.0 | acetate | 450 | 1.0/1.0 |
|  | 500 | 1.1/1.2 |  | 500 | 1.1/1.0 |
|  | 550 | 1.0/1.1 |  | 550 | 1.0/1.1 |
|  | 600 | 1.1/1.1 |  | 600 | 1.1/1.1 |
|  | 650 | 1.2/1.0 |  | 650 | 1.2/1.0 |
| Dioxane | 400 | 1.0/1.0 | Isobutyl | 400 | 1.0/1.0 |
|  | 450 | 1.0/1.0 | acetate | 450 | 0.9/0.9 |
|  | 500 | 1.1/1.0 |  | 500 | 1.1/1.1 |
|  | 550 | 1.2/1.1 |  | 550 | 0.9/1.0 |
|  | 600 | 1.1/1.0 |  | 600 | 1.1/1.1 |
|  | 650 | 1.0/1.0 |  | 650 | 1.1/1.0 |
| Diisobutyl ether | 400 | 1.1/1.0 | Methyl aceto- acetate | 400 | 1.0/0.9 |
|  | 450 | 1.0/1.0 |  | 450 | 1.0/1.0 |
|  | 500 | 1.1/1.1 |  | 500 | 1.1/1.0 |
|  | 550 | 1.2/1.1 |  | 550 | 0.9/1.0 |
|  | 600 | 1.1/1.0 |  | 600 | 1.1/1.0 |
|  | 650 | 1.0/1.0 |  | 650 | 1.0/1.0 |
| 2,5-DMeTHF | 400 | 1.0/1.0 | 1:1 mixture of 2MeTHF and 2,5- DMeTHF | 400 | 1.0/1.0 |
|  | 450 | 1.0/1.1 |  | 450 | 1.0/1.0 |
|  | 500 | 1.2/1.1 |  | 500 | 1.0/1.0 |
|  | 550 | 1.1/1.0 |  | 550 | 1.1/1.0 |
|  | 600 | 1.2/1.1 |  | 600 | 1.1/1.0 |
|  | 650 | 1.1/1.2 |  | 650 | 1.0/1.0 |
| Ethyl acetate | 400 | 1.1/1.0 | Isopropyl acetate | 400 | 1.0/1.0 |
|  | 450 | 1.0/1.0 |  | 450 | 1.1/1.0 |
|  | 500 | 1.1/1.0 |  | 500 | 1.0/1.1 |
|  | 550 | 1.0/1.0 |  | 550 | 1.0/1.1 |
|  | 600 | 1.1/1.1 |  | 600 | 1.0/1.0 |
|  | 650 | 1.1/1.0 |  | 650 | 1.0/1.1 |
| Pentyl acetate | 400 | 0.9/1.0 | Isopentyl acetate | 400 | 1.0/0.9 |
|  | 450 | 1.1/1.0 |  | 450 | 1.1/1.1 |
|  | 500 | 1.1/1.1 |  | 500 | 1.2/1.1 |
|  | 550 | 1.1/1.0 |  | 550 | 1.0/1.1 |
|  | 600 | 1.2/1.0 |  | 600 | 1.1/1.0 |
|  | 650 | 1.2/1.2 |  | 650 | 1.1/1.0 |
| Ethyl aceto- acetate | 400 | 0.9/1.0 |  |  |  |
|  | 450 | 1.0/1.2 |  |  |  |
|  | 500 | 1.0/1.0 |  |  |  |
|  | 550 | 1.0/1.0 |  |  |  |
|  | 600 | 1.0/1.0 |  |  |  |
|  | 650 | 0.8/0.8 |  |  |  |

THF = tetrahydrofuran, DMP = dimethoxypropane
DMM = dimethoxymethane, 2MeTHF = 2-methyltetrahydrofuran
2,5-DMeTHF = 2,5-dimethyltetrahydrofuran

TABLE 6

| Solvent | Substrate temperature (°C.) | Ti/(Ba + Sr) ratio in film | Solvent | Substrate temperature (°C.) | Ti/(Ba + Sr) ratio in film |
|---|---|---|---|---|---|
| Raw materials: Ba(DPM)$_2$ + Sr(DPM)$_2$ + TiO(DPM)$_2$ (Comparative Examples) | | | | | |
| THF | 400 | <0.1/0.1 | DMP | 400 | 0.1/1.8 |
| | 450 | <0.1/0.1 | | 450 | 0.2/1.2 |
| | 500 | 1.0/0.2 | | 500 | 0.1/1.6 |
| | 550 | 1.0/0.1 | | 550 | 0.5/1.5 |
| | 600 | 1.0/0.1 | | 600 | 0.1/0.9 |
| | 650 | 0.3/0.1 | | 650 | 0.2/0.9 |
| DMP | 400 | 0.1/1.3 | | | |
| | 450 | 1.0/0.1 | | | |
| | 500 | 0.3/1.5 | | | |
| | 550 | 0.5/1.2 | | | |
| | 600 | 0.1/1.8 | | | |
| | 650 | 0.1/0.9 | | | |
| Raw materials: Ba(DPM)$_2$ + Sr(DPM)$_2$ + Ti(DPM)$_2$(O-i-Pr)$_2$ (Comparative Examples) | | | | | |
| THF | 400 | <0.1/<0.1 | DMM | 400 | <0.1/<0.1 |
| | 450 | <0.1/<0.1 | | 450 | <0.1/<0.1 |
| | 500 | 0.5/0.1 | | 500 | 0.1/<0.1 |
| | 550 | 0.8/0.1 | | 550 | 0.3/<0.1 |
| | 600 | 0.8/0.1 | | 600 | 0.3/0.1 |
| | 650 | 0.5/0.2 | | 650 | 0.3/<0.1 |
| DMP | 400 | <0.1/<0.1 | | | |
| | 450 | <0.1/<0.1 | | | |
| | 500 | <0.1/<0.1 | | | |
| | 550 | 0.2/<0.1 | | | |
| | 600 | 0.1/<0.1 | | | |
| | 650 | 0.2/<0.1 | | | |

THF = tetrahydrofuran, DMP = dimethoxypropane,
DMM = dimethoxymethane

As shown in Tables 4 and 5, when an organic titanium compound in accordance with the present invention is used as a titanium source, a BST thin film containing metals with a desired atomic ratio (Ba/Sr=1,1 that is, Ba:Sr:Ti=1:1:2) can be formed at various temperatures. Thus, the compound can effectively control the composition of the film. The results illustrate that the titanium complexes used in the present invention are stable in solution and vapor and not reactive with Sr and B sources, hence the stable compound is fed into a deposition chamber. The step covering ratio b/a was measured as in Example 3, and was 0.8 or more, that is, near 1 in all the solvents used. Thus, the compound also has superior step covering characteristics.

In contrast, as shown in Table 6, when TiO(DPM)$_2$ is used as a Ti source, the atomic ratio of the BST thin film significantly deviates from that in the raw materials [(Ba+Sr)/Ti=1/1]. Thus, the composition of the film is readily not controlled. The step-covering ratio b/a was in a range of 0.1 to 0.3 and thus step covering characteristics are inferior. The film deposition rate was significantly low.

Figure 5:
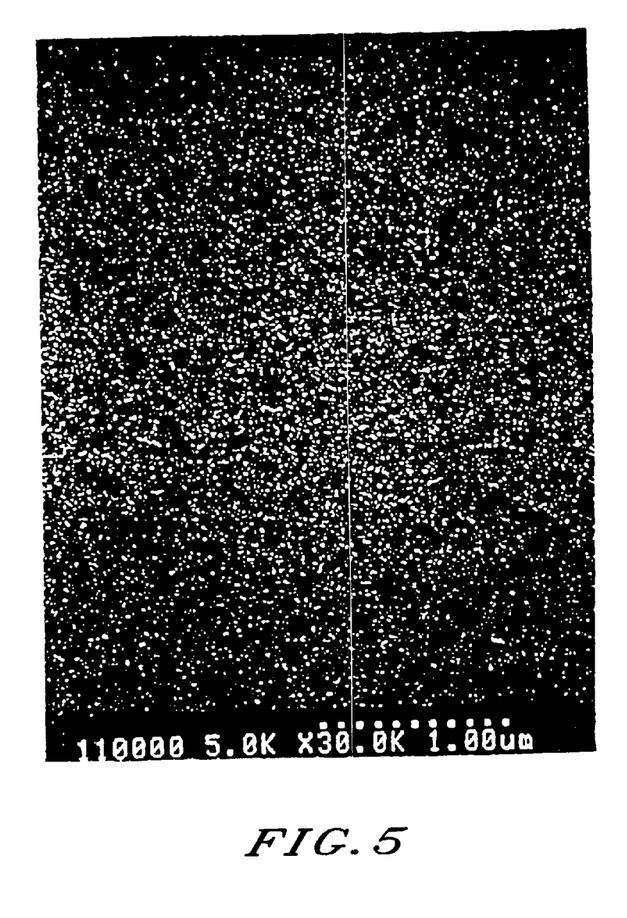
FIG. 5 is an electron microscopic photograph showing a fine texture of a BST thin film deposited using bis (dipivaloylmethanato)-diisobutoxytitanium in accordance with the present invention as a titanium source.
Figure 6:
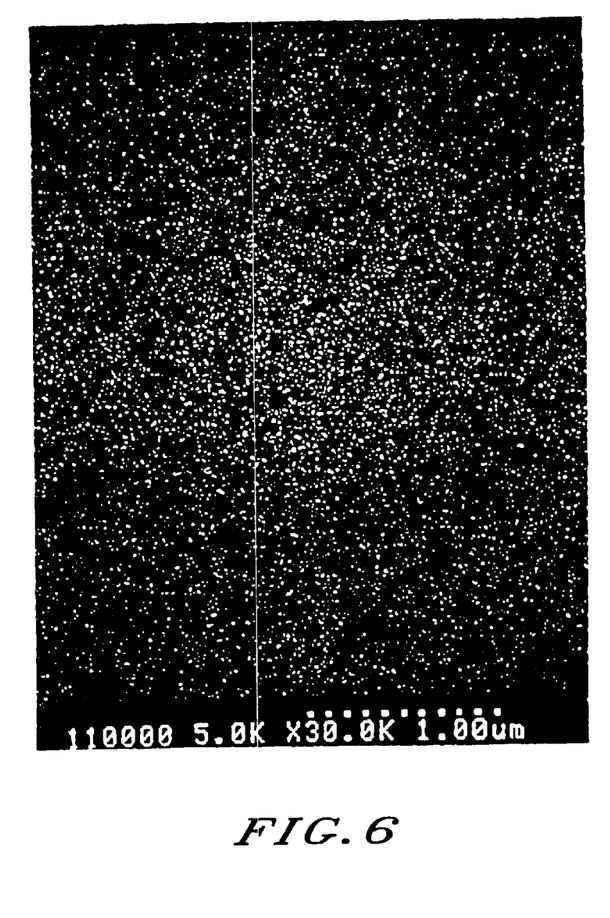
FIG. 6 is an electron microscopic photograph showing a fine texture of a BST thin film deposited using bis (dipivaloylmethanato)-di(2,2-dimethyl-1-propoxytitanlum in accordance with the present invention as a titanium source.

The fine texture of the BST thin film formed using the organic titanium compound in accordance with the present invention was observed with an electron microscopic photograph. Crystal grains were observed as granules in a photograph with a 1-μm scale when any solvents are used. The crystal grain size was several tens of nm or less, and was significantly fine and uniform. Examples of photographs when the organic titanium compounds in accordance with the present invention are shown in FIG. 5 for Ti(DPM)$_2$(O-i-Bu)$_2$ and FIG. 6 for Ti(DPM)$_2$(O-DMPr)$_2$.

Figure 7A:
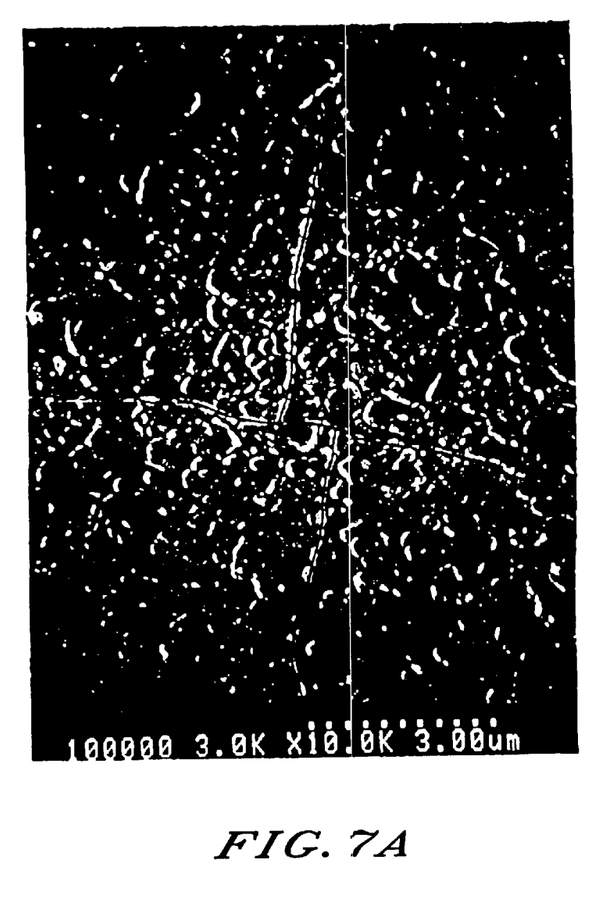
Figure 7B:
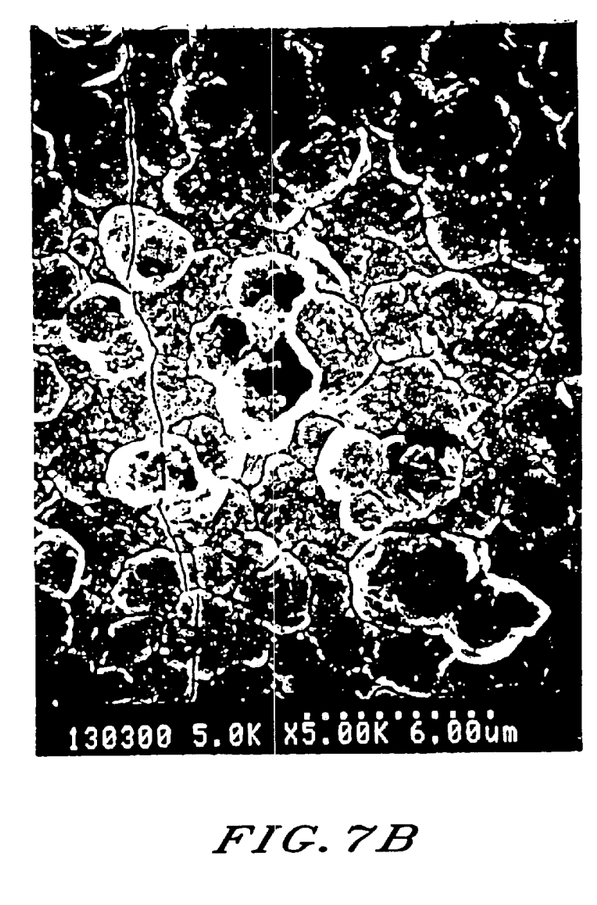

For comparison, the electron microscopic photographs of BST thin films deposited using Ti(DPM)$_2$(O-i-Pr)$_2$ and Ti(DPM)$_2$ as titanium sources are shown in FIG. 7(a) (scale: 3 μm) and FIG. 7(b) (scale: 6 μm), respectively. The BST thin film shown in FIG. 7(a) using Ti(DPM)$_2$(O-i-Pr)$_2$ as a titanium source has significantly coarser crystal grains compared with the BST thin films using the titanium compounds in accordance with the present invention, and has cracks. The BST thin film shown in FIG. 7(b) using Ti(DPM)$_2$ as a titanium source has more significantly coarser crystal grains and cracks. Such dielectric thin films having coarse crystal grains and cracks do not show desired characteristics, and reliability of the films is significantly decreased.

EXAMPLE 6

BST films were formed using Ba(DPM)$_2$.TEG and Sr(DPM)$_2$.TEG as a Ba source and a Sr source as in Example 5. That is organic titanium compounds Ti(DPM)$_2$(O-i-Bu)$_2$ of Example 1 and Ti(DPM)$_2$(O-DMPr)$_2$ of Example 2 were used as Ti sources. The analytical results of the compositions of the BST films are shown in Table 7 for Ti(DPM)$_2$ (O-i-Bu)$_2$ and Table 8 for Ti(DPM)$_2$(O-DMPr)$_2$.

For comparison, BST films were similarly formed using known TiO(DPM)$_2$ and TiO(DPM)$_2$(O-i-Pr)$_2$. The results are shown in Table 9.

TABLE 7

Raw materials: Ba(DPM)$_2$ .TEG + Sr(DPM)$_2$ .TEG + Ti(DPM)$_2$(O-i-Bu)$_2$ (Examples)

| Solvent | Substrate temperature (°C.) | Ti/(Ba + Sr) ratio in film | Solvent | Substrate temperature (°C.) | Ti/(Ba + Sr) ratio in film |
|---|---|---|---|---|---|
| THF | 400 | 1.0/1.0 | DMP | 400 | 1.0/1.0 |
| | 450 | 1.0/1.0 | | 450 | 1.0/1.0 |
| | 500 | 1.1/1.2 | | 500 | 1.1/1.1 |
| | 550 | 1.1/1.0 | | 550 | 1.1/1.2 |
| | 600 | 1.1/1.2 | | 600 | 1.0/1.1 |
| | 650 | 1.1/1.1 | | 650 | 1.0/1.1 |
| Pyridine | 400 | 1.0/1.1 | Lutidine | 400 | 1.0/1.1 |
| | 450 | 1.2/1.1 | | 450 | 1.0/1.0 |
| | 500 | 1.2/1.1 | | 500 | 1.1/1.0 |
| | 550 | 1.1/1.2 | | 550 | 0.9/1.0 |
| | 600 | 1.0/1.0 | | 600 | 0.8/1.0 |
| | 650 | 1.0/1.1 | | 650 | 0.9/1.0 |
| Isooctane | 400 | 1.0/1.1 | Butyl acetate | 400 | 1.0/1.0 |
| | 450 | 1.0/1.1 | | 450 | 1.1/1.1 |
| | 500 | 1.0/1.1 | | 500 | 1.1/1.0 |
| | 550 | 1.0/1.2 | | 550 | 1.0/1.1 |

TABLE 7-continued

Raw materials: Ba(DPM)$_2$ .TEG + Sr(DPM)$_2$ .TEG + Ti(DPM)$_2$(O-i-Bu)$_2$ (Examples)

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|
|  | 600 | 1.0/1.0 |  | 600 | 1.0/1.0 |
|  | 650 | 1.0/1.1 |  | 650 | 1.0/1.1 |
| Octane | 400 | 1.0/1.0 | Cyclo- | 400 | 1.0/1.0 |
|  | 450 | 1.0/1.0 | hexane | 450 | 1.1/1.1 |
|  | 500 | 1.0/1.0 |  | 500 | 1.0/1.0 |
|  | 550 | 1.1/1.1 |  | 550 | 1.0/1.1 |
|  | 600 | 1.0/1.1 |  | 600 | 1.0/1.0 |
|  | 650 | 1.0/1.0 |  | 650 | 1.0/1.0 |
| DMM | 400 | 1.1/1.0 | 2MeTHF | 400 | 1.1/1.1 |
|  | 450 | 1.1/1.1 |  | 450 | 1.2/1.0 |
|  | 500 | 1.1/1.2 |  | 500 | 1.1/1.1 |
|  | 550 | 1.1/1.0 |  | 550 | 1.0/1.1 |
|  | 600 | 1.0/1.1 |  | 600 | 1.0/1.0 |
|  | 650 | 1.1/1.2 |  | 650 | 1.0/1.2 |
| Hexane | 400 | 1.1/1.1 | Methyl | 400 | 1.1/1.1 |
|  | 450 | 1.2/1.0 | acetate | 450 | 1.2/1.0 |
|  | 500 | 1.1/1.1 |  | 500 | 1.1/1.1 |
|  | 550 | 1.0/1.1 |  | 550 | 1.0/1.1 |
|  | 600 | 1.1/1.0 |  | 600 | 1.1/1.0 |
|  | 650 | 1.0/1.2 |  | 650 | 1.0/1.0 |
| Dioxane | 400 | 1.2/1.1 | Isobutyl | 400 | 1.0/1.1 |
|  | 450 | 1.0/1.2 | acetate | 450 | 1.0/1.0 |
|  | 500 | 1.1/1.0 |  | 500 | 1.1/1.0 |
|  | 550 | 1.0/1.1 |  | 550 | 0.9/1.0 |
|  | 600 | 1.1/1.1 |  | 600 | 0.9/1.0 |
|  | 650 | 1.0/1.0 |  | 650 | 1.0/1.0 |
| Diisobutyl | 400 | 1.2/1.1 | Methyl | 400 | 1.0/1.1 |
| ether | 450 | 1.0/1.0 | aceto- | 450 | 1.0/1.2 |
|  | 500 | 1.1/1.0 | acetate | 500 | 1.1/1.0 |
|  | 550 | 1.0/1.1 |  | 550 | 1.0/1.1 |
|  | 600 | 1.1/1.1 |  | 600 | 1.1/1.0 |
|  | 650 | 1.0/1.0 |  | 650 | 1.0/1.0 |
| 2,5-DMeTHF | 400 | 1.0/1.0 | 1:1 | 400 | 1.0/1.0 |
|  | 450 | 0.9/1.0 | mixture | 450 | 1.0/1.0 |
|  | 500 | 1.1/1.2 | of | 500 | 1.1/1.2 |
|  | 550 | 0.9/1.0 | 2MeTHF | 550 | 1.1/1.0 |
|  | 600 | 1.0/1.1 | and 2,5- | 600 | 1.1/1.1 |
|  | 650 | 1.1/1.1 | DMeTHF | 650 | 1.1/1.1 |
| Ethyl | 400 | 1.0/1.0 | Isopropyl | 400 | 1.0/1.0 |
| acetate | 450 | 1.0/1.0 | acetate | 450 | 1.2/1.1 |
|  | 500 | 1.1/1.0 |  | 500 | 1.2/1.1 |
|  | 550 | 1.1/1.2 |  | 550 | 1.0/1.1 |
|  | 600 | 1.0/1.1 |  | 600 | 1.0/1.0 |
|  | 650 | 1.0/1.1 |  | 650 | 1.0/1.0 |
| Pentyl | 400 | 1.1/1.0 | Isopentyl | 400 | 1.0/1.0 |
| acetate | 450 | 1.1/1.1 | acetate | 450 | 0.9/1.1 |
|  | 500 | 1.1/1.0 |  | 500 | 1.1/1.0 |
|  | 550 | 1.1/1.0 |  | 550 | 1.0/1.0 |
|  | 600 | 1.0/1.1 |  | 600 | 1.0/1.0 |
|  | 650 | 1.1/1.1 |  | 650 | 1.1/0.9 |
| Ethyl | 400 | 1.0/1.0 |  |  |  |
| aceto- | 450 | 1.0/1.1 |  |  |  |
| acetate | 500 | 1.0/1.1 |  |  |  |
|  | 550 | 1.0/0.9 |  |  |  |
|  | 600 | 1.0/1.0 |  |  |  |
|  | 650 | 1.0/1.1 |  |  |  |

THF = tetrahydrofuran, DMP = dimethoxypropane
DMM = dimethoxymethane, 2MeTHF = 2-methyltetrahydrofuran
2,5-DMeTHF = 2,5-dimethyltetratrahydrofuran

TABLE 8

Raw materials: Ba(DPM)$_2$.TEG + Sr(DPM)$_2$.TEG + Ti(DPM)$_2$
(Examples)

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|
| THF | 400 | 1.1/1.0 | SMP | 400 | 1.1/1.1 |
|  | 450 | 1.0/1.1 |  | 450 | 1.0/1.0 |
|  | 500 | 1.1/1.1 |  | 500 | 1.0/1.0 |
|  | 550 | 1.2/1.1 |  | 550 | 1.1/1.2 |
|  | 600 | 1.1/1.0 |  | 600 | 1.1/1.0 |
|  | 650 | 1.0/1.1 |  | 650 | 1.1/1.1 |
| Pyridine | 400 | 1.0/1.0 | Lutidine | 400 | 1.0/1.1 |
|  | 450 | 1.2/1.1 |  | 450 | 1.0/1.0 |
|  | 500 | 1.2/1.1 |  | 500 | 1.1/1.1 |
|  | 550 | 1.1/1.0 |  | 550 | 0.9/1.0 |
|  | 600 | 1.0/1.0 |  | 600 | 0.9/0.9 |
|  | 650 | 1.0/1.0 |  | 650 | 0.9/0.8 |
| Isooctane | 400 | 1.0/1.1 | Butyl acetate | 400 | 1.0/1.1 |
|  | 450 | 1.0/1.1 |  | 450 | 1.1/1.1 |
|  | 500 | 1.0/1.0 |  | 500 | 1.0/1.0 |
|  | 550 | 1.1/1.0 |  | 550 | 1.1/1.0 |
|  | 600 | 1.0/1.0 |  | 600 | 1.0/1.0 |
|  | 650 | 1.0/1.1 |  | 650 | 1.1/1.0 |
| Octane | 400 | 1.0/1.1 | Cyclohexane | 400 | 1.0/1.1 |
|  | 450 | 1.0/1.0 |  | 450 | 0.9/1.0 |
|  | 500 | 1.0/1.0 |  | 500 | 1.0/1.0 |
|  | 550 | 1.1/1.1 |  | 550 | 1.0/1.0 |
|  | 600 | 1.1/1.0 |  | 600 | 1.0/1.0 |
|  | 650 | 1.1/1.1 |  | 650 | 1.1/1.0 |
| DMM | 400 | 1.0/1.0 | 2 MeTHF | 400 | 1.1/1.1 |
|  | 450 | 1.1/1.0 |  | 450 | 1.1/1.0 |
|  | 500 | 1.0/1.0 |  | 500 | 0.9/1.0 |
|  | 550 | 1.1/1.1 |  | 550 | 1.0/1.1 |
|  | 600 | 1.0/1.1 |  | 600 | 1.0/0.9 |
|  | 650 | 1.2/1.0 |  | 650 | 1.0/1.2 |
| Hexane | 400 | 1.1/1.1 | Methyl acetate | 400 | 1.1/1.1 |
|  | 450 | 1.1/1.1 |  | 450 | 1.1/1.0 |
|  | 500 | 1.1/1.1 |  | 500 | 1.1/1.1 |
|  | 550 | 1.0/1.1 |  | 550 | 1.0/1.1 |
|  | 600 | 1.0/0.9 |  | 600 | 1.0/0.9 |
|  | 650 | 1.0/1.2 |  | 650 | 1.0/1.2 |
| Dioxane | 400 | 1.1/1.1 | Isobutyl acetate | 400 | 1.0/1.0 |
|  | 450 | 1.0/1.0 |  | 450 | 1.0/1.0 |
|  | 500 | 1.1/1.1 |  | 500 | 1.1/1.1 |
|  | 550 | 1.0/1.2 |  | 550 | 0.9/1.0 |
|  | 600 | 1.1/1.2 |  | 600 | 0.9/0.9 |
|  | 650 | 1.1/1.1 |  | 650 | 0.9/0.8 |
| Diisobutyl ether | 400 | 1.1/1.1 | Methyl acetoacetate | 400 | 1.1/1.0 |
|  | 450 | 1.0/1.0 |  | 450 | 1.0/1.0 |
|  | 500 | 1.0/1.1 |  | 500 | 1.1/1.1 |
|  | 550 | 1.0/1.2 |  | 550 | 1.0/1.2 |
|  | 600 | 1.1/1.1 |  | 600 | 1.0/1.1 |
|  | 650 | 1.1/1.1 |  | 650 | 1.1/1.1 |
| 2,5-DMeTHF | 400 | 1.0/1.0 | 1:1 mixture of 2 MeTHF and 2,5-DMeTHF | 400 | 1.0/1.0 |
|  | 450 | 1.0/0.9 |  | 450 | 1.0/1.1 |
|  | 500 | 1.0/1.0 |  | 500 | 1.1/1.1 |
|  | 550 | 1.1/1.0 |  | 550 | 1.2/1.0 |
|  | 600 | 1.0/1.1 |  | 600 | 1.1/1.0 |
|  | 650 | 1.0/1.0 |  | 650 | 1.0/1.1 |
| Ethyl acetate | 400 | 1.1/1.0 | Isopropyl acetate | 400 | 1.0/1.0 |
|  | 450 | 1.0/1.0 |  | 450 | 1.2/1.1 |
|  | 500 | 1.0/1.0 |  | 500 | 1.2/1.1 |
|  | 550 | 1.1/1.1 |  | 550 | 1.0/1.0 |
|  | 600 | 1.1/1.0 |  | 600 | 1.0/1.0 |
|  | 650 | 1.1/1.1 |  | 650 | 1.0/0.9 |
| Pentyl acetate | 400 | 0.9/1.0 | Isopentyl acetate | 400 | 1.0/1.1 |
|  | 450 | 1.1/1.0 |  | 450 | 1.1/1.1 |
|  | 500 | 0.9/1.0 |  | 500 | 1.0/1.0 |
|  | 550 | 1.1/1.1 |  | 550 | 1.0/1.0 |
|  | 600 | 1.0/1.1 |  | 600 | 1.0/1.0 |
|  | 650 | 1.1/1.0 |  | 650 | 1.1/1.0 |
| Ethyl acetoacetate | 400 | 1.0/0.9 |  |  |  |
|  | 450 | 1.0/1.1 |  |  |  |
|  | 500 | 1.1/1.0 |  |  |  |
|  | 550 | 1.1/1.0 |  |  |  |
|  | 600 | 1.0/1.0 |  |  |  |
|  | 650 | 1.0/0.9 |  |  |  |

TABLE 8-continued

Raw materials: Ba(DPM)$_2$.TEG + Sr(DPM)$_2$.TEG + Ti(DPM)$_2$
(Examples)

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|

THF = tetrahydrofuran, DMP = dimethoxypropane
DMM = dimethoxymethane, 2 MeTHF = 2-methyltetrahydrofuran
2,5-DMeTHF = 2,5-dimethyltetrahydrofuran

TABLE 9

| Solvent | Substrate temperature (° C.) | Ti/(Ba + Sr) ratio in film | Solvent | Substrate temperature (° C.) | Ti/(Ba + Sr) ratio in film |
|---|---|---|---|---|---|
| Raw materials: Ba(DPM)$_2$.TEG + Sr(DPM)$_2$.TEG + TiO(DPM)$_2$ (Comparative Examples) | | | | | |
| THF | 400 | 1.2/<0.1 | DMM | 400 | 0.1/1.5 |
|  | 450 | 1.5/0.1 |  | 450 | 0.1/1.2 |
|  | 500 | 1.0/0.3 |  | 500 | 0.2/1.0 |
|  | 550 | 1.4/<0.1 |  | 550 | 0.4/1.0 |
|  | 600 | 1.3/<0.1 |  | 600 | 0.1/1.5 |
|  | 650 | 1.0/<0.1 |  | 650 | 0.2/1.8 |
| DMP | 400 | 0.1/1.3 |  |  |  |
|  | 450 | 0.1/1.0 |  |  |  |
|  | 500 | 0.2/1.2 |  |  |  |
|  | 550 | 0.1/1.0 |  |  |  |
|  | 600 | 0.3/1.8 |  |  |  |
|  | 650 | 0.4/1.5 |  |  |  |
| Raw materials: Ba(DPM)$_2$.TEG + Sr(DPM)$_2$.TEG + Ti(DMP)$_2$(O-i-Pr)$_2$ (Comparative Example) | | | | | |
| THF | 400 | 1.8/<0.1 | DMM | 400 | 1.2/0.1 |
|  | 450 | 1.0/<0.1 |  | 450 | 1.0/0.3 |
|  | 500 | 0.7/<0.1 |  | 500 | 0.9/0.1 |
|  | 550 | 0.7/<0.1 |  | 550 | 1.2/0.5 |
|  | 600 | 0.9/<0.1 |  | 600 | 1.6/0.4 |
|  | 650 | 0.6/0.1 |  | 650 | 1.8/0.2 |
| DMP | 400 | 0.1/1.8 |  |  |  |
|  | 450 | 0.1/1.6 |  |  |  |
|  | 500 | 0.3/1.2 |  |  |  |
|  | 550 | 0.9/0.1 |  |  |  |
|  | 600 | 0.3/1.5 |  |  |  |
|  | 650 | 0.2/1.6 |  |  |  |

THF = tetrahydrofuran, DMP = dimethoxypropane, DMM = dimethoxymethane

As shown in Tables 7 to 9 results of film deposition similar to those in Example 5 are obtained when the Ba and Sr sources are replaced. That is, when Ti(DPM)$_2$(O-i-Bu)$_2$ or Ti(DPM)$_2$(O-DMPr)$_2$ in accordance with the present invention is used as a Ti source, a BST thin film having a composition near the atomic ratio of the raw materials is formed. Thus, the film can control the composition. The step covering characteristics and the thickness were similar to those in Example 5.

In contrast, the conventional titanium complex as a titanium source causes a large fluctuation in the film thickness. Thus, the thickness cannot be controlled.

The advantage of the present invention is that a novel titanium complex in accordance with the present invention has a low vaporization temperature, is stable in solution and vapor, and is rapidly decomposed at lower than 280° C.; hence it is suitable for a titanium source in the production of a dielectric thin film by a MOCVD process. When the titanium complex in accordance with the present invention is used, a dielectric thin film having a thickness which is substantially proportional to the deposition time and the concentration of the raw materials in the solution; hence the thickness can be readily and precisely controlled and the deposition rate can be significantly increased compared to conventional processes. A dielectric thin film allowing readily controlling the film composition and having superior step covering characteristics can be formed over a significantly wide temperature range from a low temperature to a high temperature. Accordingly, the present invention contributes to both improvements in characteristics of BST and other dielectric thin films and effective formation of thin films.

The disclosure of Japanese priority applications Hei 10-027241, filed Feb. 9, 1998; Hei 10-027243, filed Feb. 9, 1998; and Hei 10-059581, filed Mar. 11, 1998, are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A method of forming a titanate thin film, comprising:
subjecting a stock solution comprising an organic titanium compound represented by the general formula $Ti(DPM)_2(OR)_2$ dissolved in an organic solvent to a metal-organic chemical vapor deposition process on a substrate thereby forming said film;
wherein in said formula DPM represents dipivaloylmethanato and R represents a neopentyl group.

2. The method of forming a titanate thin film according to claim 1, wherein the organic solvent is at least one solvent selected from the group consisting of a cyclic alkane, an acyclic alkane, a cyclic monoether, an acyclic monoether, a cyclic diether, an acyclic diether, an alkoxyalcohol, a diol, an ester, a substituted pyridine and an unsubstituted pyridine.

3. A titanate thin film deposited on a substrate by a method according to claim 2.

4. The method of forming a titanate thin film according to claim 1, wherein said organic solvent is at least one solvent selected from the group consisting of a cyclic or acyclic alkane having 5 to 8 carbon atoms, a dioxane, an acyclic diether having 3 to 12 carbon atoms, an unsubstituted tetrahydrofuran, a lower alkylsubstitued tetrahydrofuran, a mono- or di-branched alkylether having 5 to 12 carbon atoms, an alkoxyalcohol having 3 to 12 carbon atoms, a diol having 2 to 4 carbon atoms, an alkyl acetate wherein the alkyl has 1 to 5 carbon atoms and an alkyl acetoacetate wherein the alkyl has 1 to 5 carbon atoms.

5. A titanate thin film deposited on a substrate by a method according to claim 4.

6. The method of forming a titanate thin film according to claim 1, wherein the organic solvent is monomethyl- or dimethylsubstituted tetrahydrofuran.

7. A titanate thin film deposited on a substrate by a method according to claim 6.

8. A titanate thin film deposited on a substrate by a method according to claim 1.

9. A barium strontium titanate thin film deposited on a substrate obtained by a method comprising subjecting a stock solution comprising (1) an organic titanium compound represented by the general formula $Ti(DPM)_2(OR)_2$ wherein DPM represents dipivaloylmethanato and R represents a neopentyl group, (2) a barium source, and (3) a strontium source, dissolved in an organic solvent, to a metal-organic chemical vapor deposition process on a substrate, thereby forming said film.

10. The barium strontium titanate thin film deposited on a substrate according to claim 9, wherein the organic solvent is at least one solvent selected from the group consisting of cyclic and acyclic alkanes, cyclic and acyclic monoethers and diethers, alkoxyalcohols, diols, esters, and substituted and unsubstituted pyridines.

11. The barium strontium titanate thin film deposited on a substrate according to claim 10, wherein the organic solvent is at least one solvent selected from the group consisting of cyclic and acyclic alkanes having 5 to 8 carbon atoms, dioxane, acyclic diethers having 3 to 12 carbon atoms, unsubstituted and lower alkylsubstituted tetrahydrofurans, mono- and di-branched alkylethers having 5 to 12 carbon atoms, alkoxyalcohols having 3 to 12 carbon atoms, diols having 2 to 4 carbon atoms, alkyl acetates and alkyl acetoacetates wherein the alkyl has 1 to 5 carbon atoms, pyridine, and lower alkyl-substituted pyridines.

12. The barium strontium titanate thin film deposited on a substrate according to claim 11, wherein the organic solvent is monomethyl- or dimethylsubstituted tetrahydrofuran.

13. A method of forming a titanate thin film, comprising:
subjecting an organic titanium compound represented by the general formula $Ti(DPM)_2(OR)_2$ wherein DPM represents dipivaloylmethanato and R represents a neopentyl group, to a metal-organic chemical vapor deposition process on a substrate, thereby forming said film.

* * * * *